US006777231B1

(12) United States Patent
Katz et al.

(10) Patent No.: US 6,777,231 B1
(45) Date of Patent: Aug. 17, 2004

(54) ADIPOSE-DERIVED STEM CELLS AND LATTICES

(75) Inventors: Adam J. Katz, Charlottesville, VA (US); Ramon Llull, Mallorca (ES); William J. Futrell, Pittsburgh, PA (US); Marc H. Hedrick, Encino, CA (US); Prosper Benhaim, Los Angeles, CA (US); Hermann Peter Lorenz, Los Angeles, CA (US); Min Zhu, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/936,665

(22) PCT Filed: Mar. 10, 2000

(86) PCT No.: PCT/US00/06232

§ 371 (c)(1),
(2), (4) Date: Sep. 10, 2001

(87) PCT Pub. No.: WO00/53795

PCT Pub. Date: Sep. 14, 2000

Related U.S. Application Data

(60) Provisional application No. 60/123,711, filed on Mar. 10, 1999, and provisional application No. 60/162,462, filed on Oct. 29, 1999.

(51) Int. Cl.[7] ............................. C12N 5/00; C12N 5/08
(52) U.S. Cl. ....................................... 435/325; 435/366
(58) Field of Search .................................. 435/325, 366

(56) References Cited

U.S. PATENT DOCUMENTS

| | | | |
|---|---|---|---|
| 5,226,914 A | | 7/1993 | Caplan et al. |
| 5,486,359 A | * | 1/1996 | Caplan et al. .............. 424/93.7 |
| 5,591,625 A | | 1/1997 | Gerson et al. |
| 5,728,739 A | * | 3/1998 | Ailhaud et al. .............. 514/725 |
| 5,736,396 A | | 4/1998 | Bruder et al. |
| 5,786,207 A | | 7/1998 | Katz et al. |
| 5,811,094 A | | 9/1998 | Caplan et al. |
| 5,817,050 A | | 10/1998 | Klein |
| 5,827,735 A | | 10/1998 | Young et al. |
| 5,827,740 A | * | 10/1998 | Pittenger et al. ............ 435/372 |
| 5,827,897 A | | 10/1998 | Ailhaud et al. |
| 5,854,292 A | * | 12/1998 | Ailhaud et al. .............. 514/725 |
| 5,908,784 A | | 6/1999 | Johnstone et al. |

FOREIGN PATENT DOCUMENTS

| | | | | |
|---|---|---|---|---|
| WO | WO97/18299 | 5/1997 | | |
| WO | WO97/39104 | 10/1997 | | |
| WO | WO97/40137 | 10/1997 | | |
| WO | WO97/41208 | 11/1997 | | |
| WO | WO 98/04682 | * 2/1998 | ............. | 435/372.3 |
| WO | WO98/32333 | 7/1998 | | |
| WO | WO98/51317 | 11/1998 | | |
| WO | WO99/01145 | 1/1999 | | |
| WO | WO 99/02654 | 1/1999 | | |
| WO | WO99/03973 | 1/1999 | | |
| WO | WO99/11789 | 3/1999 | | |
| WO | WO 99/28444 | 6/1999 | | |
| WO | WO 00/53795 | 9/2000 | | |
| WO | WO 01/21767 A2 | 3/2001 | | |
| WO | WO 01/62901 A2 | 8/2001 | | |

OTHER PUBLICATIONS

Zuk et al. Human adipose tissue is a source of multipotent stem cells. Molecular Biology of the Cell. vol. 13:4279–4295, 2002.*
Marko et al. Isolation of a preadipocyte cell line from rat bone marrow and differentiation to adipocytes. Endocrinology, vol. 136(10): 4582–4588, 1995.*
Vassaux et al. Proloferation and differentiation of rat adipose precursor cells in chemically defined mdium: differential action fo anti–adipogenic agents, J. Cell. Physiol. vol. 161:249–256, 1994.*
Soda et al. Adipocyte stem cell: a brief review. Int. J. Cell Cloning, vol. 1:79–84, 1983.*
Ailhaud et al. Lipoproteine lipase et differenclation adipocytaire. Reprod. Nutr. Develop. vol. 25(1B): 153–158, 1985.*
Ailhaud et al. Hormonal requirements for growth and differentiation of OB17 preadipocyte cells in vitro. Diabete & Metabolisme, vol. 9:125–133, 1983.*
Bennett, JH, et al., 1991 *J. Cell Sci.* "Adipocytic cells cultured from marrow have osteogenic potential," 99(Ptl):131–139 (Exhibit 63).
Bond et al., 1999, "Human Subcutaneouspreadipocytes Differentiate Into osteoblasts," *FASEB Journal* 13:600A (Exhibit 64).
Smith et al., 2000, "Mesenchymal Stem Cells Derived From Bone Marrow And Human Adipose Tissue Exhibit Multilineage Potential," *Journal of Investigative Medicine*, 95A. (Exhibit 65).
Stashower et al., 1999, "Stromal progenitor cells present within liposuction and reduction abdominoplasty fat for autologous transfer to aged skin," *Dermatologic Surgery*, 25:12:945–949. (Exhibit 66).

(List continued on next page.)

*Primary Examiner*—Remy Yucel
*Assistant Examiner*—William Sandals
(74) *Attorney, Agent, or Firm*—Mandel & Adriano

(57) ABSTRACT

The present invention provides adipose-derived stem cells and lattices. In one aspect, the present invention provides a lipo-derived stem cell substantially free of adipocytes and red blood cells and clonal populations of connective tissue stem cells. The cells can be employed, alone or within biologically-compatible compositions, to generate differentiated tissues and structures, both in vivo and in vitro. Additionally, the cells can be expanded and cultured to produce hormones and to provide conditioned culture media for supporting the growth and expansion of other cell populations. In another aspect, the present invention provides a lipo-derived lattice substantially devoid of cells, which includes extracellular matrix material from adipose tissue. The lattice can be used as a substrate to facilitate the growth and differentiation of cells, whether in vivo or in vitro, into anlagen or even mature tissues or structures.

10 Claims, No Drawings

OTHER PUBLICATIONS

Strutt et al., 1996, "Growth and differentiation of human adipose stromal cells in culture," *methods in Molecular Medicine: Human Cell Culture Protools*, 41–51. (Exhibit 67).

Tavassoli et al., 1981, "The Nature of Fibroblasts Derived From Adipose Tissue In–Vitro," *Clinical Research*, 29:5:871A. (Exhibit 68).

Van et al., 1978, "Complete Differentiation of Adipocyte Precursors," *Cell Tissue*, 195:317–329. (Exhibit 69).

Zuk, et al., 2001 "Multilineage cells from human adipose tissue: implications for cell–based therapies," *Tissue Engineering*, 7:211–228. (Exhibit 73).

Grigoradis A., et al., 1988 *J. Cell Biol.* "Differentiation of Muscle, Fat, Cartilage, and Bone from Progenitor Cells Present in a Bone–derived Clonal Cell Population: Effect of Dexamethasone," 106: 2139–2151 (Exhibit 60).

Considine, et al., "Paracrine stimulation of preadipocyte–enriched cell cultures by mature adipocytes," *American Journal of Physiology* 1996 270(5) E895–E899 (EXHIBIT 6).

Dani, et al., "Differentiation of embryonic stem cells into adipocytes in vitro," *J. Cell Sci.* 1997 110, 1279–1285 (EXHIBIT 7).

Entenmann, et al., "Relationship between replication and differentiation cultured human adipocyte precursor cells," *American Phys. Soc.* 1996 270, C1011–C1016 (EXHIBIT 8).

Eslami Varzaneh, et al., "Extracellular Matrix Components Secreted by Microvascular Endothelial Cells Stimulate Preadipocyte Differentiation In Vitro," *Metabolism* 1994 43 (7), 906–912 (EXHIBIT 9).

Hauner, et al., "Endothelin–1 Inhibits the Adipose Differentiation of Cultured Human Adipocyte Precursor Cells," *Metabolism* 1994 43(2) pp 227–232 (EXHIBIT 10).

Hausman, et al., "The Influence of Extracellular Matrix Substrata on Preadipocyte Development in Serum–Free Cultures of Stromal—Vascular Cells," *J. Anim. Sci.* 1996 74(9), 2117–2128 (EXHIBIT 11).

Hui–Ling et al., "Increased expression of G in mouse embryo stem cells promotes terminal differentiation to adipocytes," *American Physiological Society* 1993 265(6), C1729–C1735 (EXHIBIT 12).

Marko, et al., "Isolation of a Preadipocyte Cell Line from Rat Bone Marrow and Differentiation to Adipocytes," *Endocrinology* 1995 136(10), 4582–4588 (EXHIBIT 13).

Shillabeer, et al., "A novel method for studying preadipocyte differentiation in vitro," *Intl. J. Obesity* 1996 20(Supp. 3), S77–S83 (EXHIBIT 14).

Sorisky et al., "From preadipoctye to Adipocyte: Differentiation–Directed Signals of Insulin from the Cell Surface to the Nucleus," *Critical Review in Clinical Laboratory Sciences* 1999 36(1), 1–34 (EXHIBIT 15).

Bastard, J. P. et al., "A Mini–Liposuction Technique Adapted to the Study of Human Adipocyte Glucose Transport System," *Diabetologia*, 36(Suppl. 1): A135, 1993 (Exhibit 34).

Caplan, Arnold I., "The Messengenic Process," *Clinics in Plastic Surgery*, 21:429–35, 1994 (Exhibit 35).

Crandall, David L. et al., "Identification of Estrogen Receptor β RNA in Human Breast and Abdominal Subcutaneous Adipose Tissue," *Biochemical and Biophysical Research Communications*, 248:523–6, 1998 (Exhibit 36).

Hauner, Hans et al., "Promoting Effect of Glucocorticoids on the Differentiation of Human Adipocyte Precursor Cells Cultured in a Chemically Defined Medium," *Journal of Clinical Investigation*, 84:1663–70, 1989 (Exhibit 37).

Hauner H. et al., "Glucocorticoids and Insulin Promote the Differentiation of Human Adipocyte Precursor Cells into Fat Cells," *Journal of Clinical Endocrinology and Metabolism*, 64:832–5, 1987 (Exhibit 38).

Johnson, P. R. et al., "Uncontrolled adipocyte proliferation is not the primary lesion in the genetically–obese Zucker rat," *International Journal of Obesity*, 5:563–70, 1981 (Exhibit 39).

Killinger, D. W. et al., "Influence of Adipose Tissue Distribution on the Biological Activity of Androgens," *Annals New York Academy of Sciences*, 595:199–211, 1990 (Exhibit 40).

Killinger, Donald W. et al., "The Relationship Between Aromatase Activity and Body Fat Distribution," *Steroids*, 50:61–72, 1987 (Exhibit 41).

Lafontan, M. et al., "Réflexions sur une nouvelle approche de chirurgie plastique réparatrice: la réimplantation de fragments de tissu adipeux prélevés par liposuccion," *Ann. Chur. Plast. Esthet.*, 34:77–81, 1989 (Exhibit 42).

Lam, Anson and Ronald Moy, "The Potential for Fat Transplantation," *J. Dermatol. Surg. Oncol.*, 18:432–4, 1992 (Exhibit 43).

Lecoeur, L. and J. P. Ouhayoun, "In vitro induction of osteogenic differentiation from non–osteogenic Mesenchymal cells," *Biomaterials*, 18:989–93, 1997 (Exhibit 44).

Loncar, D., "Ultrastructural analysis of differentiatioin of rat endoderm in vitro. Adipose vascular–stromal cells induce endoderm differentiation, which in turn induces differentiation of the vascular–stromal cells into chondrocytes," *J. Submicrosc. Cytol. Pathol.*, 24:509–19, 1992 (Exhibit 45).

Novakofski, Jan E., "Primary Cell Culture of Adipose Tissue," *Biology of the Adipocyte: Research Approaches*, Van Nostrand Reinhold Company, N.Y., 1987 160–97 (Exhibit 46).

Pedersen, S. B. et al., "Identification of oestrogen receptors and oestrogen receptor mRNA in human adipose tissue," *European Journal of Clinical Investigation*, 26:262–9, 1996 (Exhibit 47).

Pettersson, Per et al., "Adipocyte Precursor Cells in Obese and Nonobese Humans," *Metabolism*, 34:808–12, 1985 (Exhibit 48).

Ramsay, T. G. et al., "Pre–Adipocyte Proliferation and Differentiation in Response to Hormone Supplementation of Decapitated Fetal Pig Sera," *J. Anim. Sci.*, 64:735–44, 1987 (Exhibit 49).

Rubens, F. D. et al., "Tissue Factor Expression by Cells Used for Sodding of Prosthetic Vascular Grafts," *Journal of Surgical Research*, 72:22–8, 1997 (Exhibit 50).

Šmahel, J., "Aspiration lipectomy and adipose tissue injection: pathophysiologic commentary," *European Journal of Plastic Surgery*, 14:126–31, 1991 (Exhibit 51).

Springhorn, Jeremy P. et al., "Human Capillary Endothelial Cells from Abdominal Wall Adipose Tissue: Isolation Using an Anti–Pecam Antibody," *In Vitro Cellular & Developmental Biology–Animal*, 31:473–81, 1995 (Exhibit 52).

Tavassoli, Mehdi, "In Vivo Development of Adipose Tissue Following Implantation of Lipid–Depleted Cultured Adipocyte," *Experimental Cell Research*, 137:55–62, 1982 (Exhibit 53).

Williams, John T. et al., "Cells Isolated from Adult Human Skeletal Muscle Capable of Differentiating into Multiple Mesodermal Phenotypes," *The American Surgeon*, 65:22–6, 1999 (Exhibit 54).

Williams, Stuart K. et al. "Liposuction–derived human fat used for vascular graft sodding contains endothelial cells and not mesothelial cells as the major cell type," *Journal of Vascular Surgery*, 19:916–23, 1994 (Exhibit 55).

Wlodarski, Krzysztof H., "Section III. Basic Science and Pathology. Properties and Origin of Osteoblasts," *Clinical Orthopaedics and Related Research*, 252:276–93, 1990 (Exhibit 56).

Vassaux, et al., "Proliferation and differentiation of Rat Adipose Precursor Cells in Chemically Defined Medium: Differential Action of Anti–adipogenic Agents," *Journal of Cellular Physiology* 1994 161(2), 249–256 (EXHIBIT 16).

Wabitsch, et al., "Biological Effects of Human Growth Hormone in Rat Adipocyte Precursor Cells and Newly Differentiated Adipocytes in primary Culture," *Metabolism* 1996 vol. 45, No. 1 pp34–42 (EXHIBIT 17).

Young et al., "Mesenchymal Stem Cells Reside Within the Connective Tissues of Many Organs," *Developmental Dynamics* 1995 202(2), 137–144 (EXHIBIT 18).

* cited by examiner

ADIPOSE-DERIVED STEM CELLS AND LATTICES

This application is a:: 371 of Application One:: PCT/US00/06232 Filing Date:: Mar. 10, 2000 Which is a::NON PROV. OF PROVISIONAL Application Two:: 60/123,711 Filing Date:: Mar. 10, 1999 And which is a:: NON PROV. OF PROVISIONAL Application Three:: 60/162,462 Filing Date:: Oct. 29, 1999

BACKGROUND OF THE INVENTION

In recent years, the identification of mesenchymal stem cells, chiefly obtained from bone marrow, has led to advances in tissue regrowth and differentiation. Such cells are pluripotent cells found in bone marrow and periosteum, and they are capable of differentiating into various mesenchymal or connective tissues. For example, such bone-marrow derived stem cells can be induced to develop into myocytes upon exposure to agents such as 5-azacytidine (Wakitani et al., *Muscle Nerve*, 18(12), 1417–26 (1995)). It has been suggested that such cells are useful for repair of tissues such as cartilage, fat, and bone (see, e.g., U.S. Pat. Nos. 5,908,784, 5,906,934, 5,827,740, 5,827,735), and that they also have applications through genetic modification (see, e.g., U.S. Pat. No. 5,591,625). While the identification of such cells has led to advances in tissue regrowth and differentiation, the use of such cells is hampered by several technical hurdles. One drawback to the use of such cells is that they are very rare (representing as few as 1/2,000,000 cells), making any process for obtaining and isolating them difficult and costly. Of course, bone marrow harvest is universally painful to the donor. Moreover, such cells are difficult to culture without inducing differentiation, unless specifically screened sera lots are used, adding further cost and labor to the use of such stem cells. Thus, there is a need for a more readily available source for pluripotent stem cells, particularly cells that can be cultured without the requirement for costly prescreening of culture materials.

Other advances in tissue engineering have shown that cells can be grown in specially-defined cultures to produce three-dimensional structures. Spacial definition typically is achieved by using various acellular lattices or matrices to support and guide cell growth and differentiation. While this technique is still in its infancy, experiments in animal models have demonstrated that it is possible to employ various acellular lattice materials to regenerate whole tissues (see, e.g., Probst et al. *BJU Int.*, 85(3), 362–7 (2000)). A suitable lattice material is secreted extracellular matrix material isolated from tumor cell lines (e.g, Engelbreth-Holm-Swarm tumor secreted matrix—"matrigell"). This material contains type IV collagen and growth factors, and provides an excellent substrate for cell growth (see, e.g., Vukicevic et al., *Exp. Cell Res*, 202(1), 1–8 (1992)). However, as this material also facilitates the malignant transformation of some cells (see, e.g., Fridman, et al., *Int. J. Cancer*, 51(5), 740–44 (1992)), it is not suitable for clinical application. While other artificial lattices have been developed, these can prove toxic either to cells or to patients when used in vivo. Accordingly, there remains a need for a lattice material suitable for use as a substrate in culturing and growing populations of cells.

BRIEF SUMMARY OF THE INVENTION

The present invention provides adipose-derived stem cells and lattices. In one aspect, the present invention provides a lipo-derived stem cell substantially free of adipocytes and red blood cells and clonal populations of connective tissue stem cells. The cells can be employed, alone or within biologically-compatible compositions, to generate differentiated tissues and structures, both in vivo and in vitro. Additionally, the cells can be expanded and cultered to produce hormones and to provide conditioned culture media for supporting the growth and expansion of other cell populations. In another aspect, the present invention provides a lipo-derived lattice substantially devoid of cells, which includes extracellular matrix material from adipose tissue. The lattice can be used as a substrate to facilitate the growth and differentiation of cells, whether in vivo or in vitro, into anlagen or even mature tissues or structures.

Considering how plentiful adipose tissue is, the inventive cells and lattice represent a ready source of pluripotent stem cells. Moreover, because the cells can be passaged in culture in an undifferentiated state under culture conditions not requiring prescreened lots of serum, the inventive cells can be maintained with considerably less expense than other types of stem cells. These and other advantages of the present invention, as well as additional inventive features, will be apparent from the accompanying drawings and in the following detailed descriptions.

DETAILED DESCRIPTION OF THE INVENTION

One aspect of the invention pertains to a lipo-derived stem cell. Preferably, the stem cell is substantially free of other cell types (e.g., adipocytes, red blood cells, other stromal cells, etc.) and extracellular matrix material; more preferably, the stem cell is completely free of such other cell types and matrix material. Preferably, the inventive cell is derived from the adipose tisue of a primate, and more preferably a higher primate (e.g, a baboon or ape). Typically, the inventive cell will be derived from human adipose tissue, using methods such as described herein.

While the inventive cell can be any type of stem cell, for use in tissue engineering, desirably the cell is of mesodermal origin. Typically such cells, when isolated, retain two or more mesodermal or mesenchymal developmental phenotypes (i.e., they are pluripotent). In particular, such cells generally have the capacity to develop into mesodermal tissues, such as mature adipose tissue, bone, various tissues of the heart (e.g., pericardium, epicardium, epimyocardium, myocardium, pericardium, valve tissue, etc.), dermal connective tissue, hemangial tissues (e.g., corpuscles, endocardium, vascular epithelium, etc.), muscle tissues (including skeletal muscles, cardiac muscles, smooth muscles, etc.), urogenital tissues (e.g., kidney, pronephros, meta- and meso-nephric ducts, metanephric diverticulum, ureters, renal pelvis, collecting tubules, epithelium of the female reproductive structures (particularly the oviducts, uterus, and vagina)), pleural and peritoneal tissues, viscera, mesodermal glandular tissues (e.g., adrenal cortex tissues), and stromal tissues (e.g., bone marrow). Of course, inasmuch as the cell can retain potential to develop into mature cells, it also can realize its developmental phenotypic potential by differentiating into an appropriate precursor cell (e.g., a preadipocyte, a premyocyte, a preosteocyte, etc.). Also, depending on the culture conditions, the cells can also exhibit developmental phenotypes such as embryonic, fetal, hematopoetic, neurogenic, or neuralgiagenic developmental phenotypes. In this sense, the inventive cell can have two or more developmental phenotypes such as adipogenic, chondrogenic, cardiogenic, dermatogenic, hematopoetic, hemangiogenic, myogenic, nephrogenic, neurogenic, neuralgiagenic, urogenitogenic, osteogenic, pericardiogenic, peritoneogenic, pleurogenic, splanchogenic, and stromal developmental phenotypes. While such cells can retain two or more of these developmental phenotypes, preferably, such cells have three or more such developmental phenotypes (e.g., four or more mesodermal or mesenchymal developmental phenotypes), and some types of inventive stem cells have a potential to acquire any mesodermal phenotppe through the process of differentiation.

The inventive stem cell can be obtained from adipose tissue by any suitable method. A first step in any such method requires the isolation of adipose tissue from the source animal. The animal can be alive or dead, so long as adipose stromal cells within the animal are viable. Typically, human adipose stromal cells are obtained from living donors, using well-recognized protocols such as surgical or suction lipectomy. Indeed, as liposuction procedures are so common, liposuction effluent is a particularly preferred source from which the inventive cells can be derived.

However derived, the adipose tissue is processed to separate stem cells from the remainder of the material. In one protocol, the adipose tissue is washed with physiologically-compatible saline solution (e.g., phosphate buffered saline (PBS)) and then vigorously agitated and left to settle, a step that removes loose mater (e.g., damaged tissue, blood, erythrocytes, etc.) from the adipose tissue. Thus, the washing and settling steps generally are repeated until the supernatant is relatively clear of debris.

The remaining cells generally will be present in lumps of various size, and the protocol proceeds using steps gauged to degrade the gross structure while minimizing damage to the cells themselves. One method of achieving this end is to treat the washed lumps of cells with an enzyme that weakens or destroys bonds between cells (e.g., collagenase, dispase, trypsin, etc.). The amount and duration of such enzymatic treatment will vary, depending on the conditions employed, but the use of such enzymes is generally known in the art. Alternatively or in conjunction with such enzymatic treatment, the lumps of cells can be degraded using other treatments, such as mechanical agitation, sonic energy, thermal energy, etc. If degradation is accomplished by enzymatic methods, it is desirable to neutralize the enzyme following a suitable period, to minimize deleterious effects on the cells.

The degradation step typically produces a slurry or suspension of aggregated cells (generally liposomes) and a fluid fraction containing generally free stromal cells (e.g., red blood cells, smooth muscle cells, endothelial cells, fibroblast cells, and stem cells). The next stage in the separation process is to separate the aggregated cells from the stromal cells. This can be accomplished by centrifugation, which forces the stromal cells into a pellet covered by supernatant. The supernatant then can be discarded and the pellet suspended in a physiologically-compatible fluid. Moreover, the suspended cells typically include erythrocytes, and in most protocols it is desirable to lyse these. Methods for selectively lysing erythrocytes are known in the art, and any suitable protocol can be employed (e.g., incubation in a hyper- or hypotonic medium). Of course, if the erythrocytes are lysed, the remaining cells should then be separated from the lysate, for example by filtration or centrifugation. Of course, regardless of whether the erythrocytes are lysed, the suspended cells can be washed, re-centrifuged, and resuspended one or more successive times to achieve greater purity. Alteratively, the cells can be separated using a cell sorter or on the basis of cell size and granularity, stem cells being relatively small and agranular. Expression of telomerase can also serve as a stem cell-specific marker. They can also be separated immunohistochemically, for example, by panning or using magnetic beads. Any of the steps and procedures for isolating the inventive cells can be performed manually, if desired. Alteratively, the process of isolating such cells can be facilitated through a suitable device, many of which are known in the art (see, e.g., U.S. Pat. No. 5,786,207).

Following the final isolation and resuspension, the cells can be cultured and, if desired, assayed for number and viability to assess the yield. Desirably the cells can be cultured without differentiation using standard cell culture media (e.g, DMEM, typically supplemented with 5–15% (e.g., 10%) serum (e.g., fetal bovine serum, horse serum, etc.). Preferably, the cells can be passaged at least five times in such medium without differentiating, while still retaining their developmental phenotype, and more preferably, the cells can be passaged at least 10 times (e.g., at least 15 times or even at least 20 times) without losing developmental phenotype. Thus, culturing the cells of the present invention without inducing differentiation can be accomplished without specially screened lots of serum, as is generally the case for mesenchymal stem cells (e.g., derived from marrow). Methods for measuring viability and yield are known in the art (e.g., trypan blue exclusion).

Following isolation, the stem cells are further separated by phenotypic identification, to identify those cells that have two or more of the aforementioned developmental phenotypes. Typically, the stromal cells are plated at a desired density such as between about 100 cells/cm$^2$ to about 100,000 cells/cm$^2$ (such as about 500 cells/cm$^2$ to about 50,000 cells/cm$^2$, or, more particuarly, between about 1,000 cells/cm$^2$ to about 20,000 cells/cm$^2$). If plated at lower densities (e.g., about 300 cells/cm$^2$), the cells can be more easily clonally isolated. For example, after a few days, cells plated at such densities will proliferate into a population.

Such cells and populations can be clonally expanded, if desired, using a suitable method for cloning cell populations. For example, a proliferated population of cells can be physically picked and seeded into a separate plate (or the well of a multi-well plate). Alternatively, the cells can be subcloned onto a multi-well plate at a statistical ratio for facilitating placing a single cell into each well (e.g., from about 0.1 to about 1 cell/well or even about 0.25 to about 0.5 cells/well, such as 0.5 cells/well). Of course, the cells can be cloned by plating them at low density (e.g, in a petri-dish or other suitable substrate) and isolating them from other cells using devices such as a cloning rings. Alternatively, where an irradiation source is available, clones can be obtained by permitting the cells to grow into a monolayer and then shielding one and irradiating the rest of cells within the monolayer. The surviving cell then will grow into a clonal population. While production of a clonal population can be expanded in any suitable culture medium, a preferred culture condition for cloning stem cells (such as the inventive stem cells or other stem cells) is about ⅔ $F_{12}$medium+20% serum (preferably fetal bovine serum) and about ⅓ standard medium that haw been conditioned with stromal cells (e.g., cells from the stromal vascular fraction of liposuction aspirate), the relative proportions being determined volumetrically).

In any event, whether clonal or not, the isolated cells can be cultured to a suitable point when their developmental phenotype can be assessed. As mentioned, the inventive cells have at least two of the aforementioned developmental phenotypes. Thus, one or more cells drawn from a given clone can be treated to ascertain whether it possesses such developmental potentials. One type of treatment is to culture the inventive cells in culture media that has been conditioned by exposure to mature cells (pr precursors thereof) of the respective type to be differentiated (e.g., media conditioned by exposure to myocytes can induce myogenic differentiation, media conditioned by exposure to heart valve cells can induce differentiation into heart valve tissue, etc.). Of course, defined media for inducing differentiation also can be employed. For example, adipogenic developmental phenotype can be assessed by exposing the cell to a medium that facilitates adipogenesis, e.g., containing a glucocorticoid (e.g., isobutyl-methylxanthine, dexamethasone, hydrocortisone, cortisone, etc.), insulin, a compound which elevates intracellular levels of cAMP (e.g., dibutyryl-cAMP, 8-CPT-cAMP (8-(4)chlorophenylthio)-adenosine 3', 5'cyclic monophosphate; 8-bromo-cAMP; dioctanoyl-cAMP, forskolin etc.), and/or a compound which inhibits degradation of cAMP (e.g., a phosphodiesterase inhibitor such as methyl isobutylxanthine, theophylline, caffeine, indomethacin, and the like). Thus, exposure of the stem cells to between about 1 $\mu$M and about 10 $\mu$M insulin in combination with about $10^{-9}$ M to about $10^{-6}$ M to (e.g., about 1 $\mu$M) dexamethasone can induce adipogenic differentiation. Such a medium also can include other agents, such as indomethicin (e.g., about 100 $\mu$M to about 200 $\mu$M, if desired, and preferably the medium is serum free. Osteogenic developmental phenotype can be assessed by exposing the cells to between about $10^{-7}$ M and about $10^{-9}$ M dexamethasone (e.g., about 1 $\mu$M) in combination with about 10 $\mu$M to about 50 $\mu$M ascorbate-2-phosphate and between about 10 nM and about 50 nM β-glycerophosphate, and the medium also can include serum (e.g., bovine serum, horse serum, etc.). Myogenic differentiation can be induced by exposing the cells to between about 10 $\mu$M and about 100 $\mu$M hydrocortisone, preferably in a serum-rich medium (e.g., containing between about 10% and about 20% serum (either bovine, horse, or a mixture thereof)). Chondrogenic differentiation can be induced by exposing the cells to between about 1 $\mu$M to about 10 $\mu$M insulin and between about 1 $\mu$M to about 10 $\mu$M transferrin, between about 1 ng/ml and 10 ng/ml transforming growth factor (TGF) β1, and between about 10 nM and about 50 nM ascorbate-2-phosphate (50 nM). For chondrogenic differentiation, preferably the cells are cultured in high density (e.g., at about several million cells/ml or using micromass culture techniques), and also in the presence of low amounts of serum (e.g., from about 1% to about 5%). The cells also can be induced to assume a developmentally more immature phenotype (e.g., a fetal or embryonic phenotype). Such induction is achieved upon exposure of the inventive cell to conditions that mimic those within fetuses and embryos. For example, the inventive cells or populations can be co-cultured with cells isolated from fetuses or embryos, or in the presence of fetal serum. Along these lines, the cells can be induced to differentiate into any of the aforementioned mesodermal lineages by co-culturing them with mature cells of the respective type, or precursors thereof. Thus, for example, myogenic differentiation can be induced by culturing the inventive cells with myocytes or precursors, and similar results can be achieved with respect to the other tissue types mentioned herein. Other methods of inducing differentiation are known in the art, and many of them can be employed, as appropriate.

After culturing the cells in the differentiating-inducing medium for a suitable time (e.g., several days to a week or more), the cells can be assayed to determine whether, in fact, they have differentiated to acquire physical qualities of a given type of cell. One measurement of differentiation per se is telomere length, undifferentiated stem cells having longer telomeres than differentiated cells; thus the cells can be assayed for the level of telomerase activity. Alternatively, RNA or proteins can be extracted from the cells and assayed (via Northern hybridization, rtPCR, Western blot analysis, etc.) for the presence of markers indicative of the desired phenotype. Of course, the cells can be assayed immunohistochemically or stained, using tissue-specific stains. Thus, for example, to assess adipogenic differentiation, the cells can be stained with fat-specific stains (e.g., oil red O, safarin red, sudan black, etc.) or probed to assess the presence of adipose-related factors (e.g., type IV collagen, PPAR-γ, adipsin, lipoprotein lipase, etc.). Similarly, ostogenesis can be assessed by staining the cells with bone-specific stains (e.g., alkaline phosphatase, von Kossa, etc.) or probed for the presence of bone-specific markers (e.g., osteocalcin, osteonectin, osteopontin, type I collagen, bone morphogenic proteins, cbfa, etc.). Myogensis can be assessed by identifyng classical morphologic changes (e.g., polynucleated cells, syncitia formation, etc.), or assessed biochemically for the presence of muscle-specific factors (e.g., myo D, myosin heavy chain, NCAM, etc.). Chondrogenesis can be determined by staining the cells using cartallge-specific stains (e.g., alcian blue) or probing the cells for the expression/production of cartilage-specific molecules (e.g., sulfated glycosaminoglycans and proteoglycans (e.g., keratin, chondroitin, etc.) in the medium, type II collagen, etc.). Other methods of assessing developmental phenotype are known in the art, and any of them is appropriate. For example, the cells can be sorted by size and granularity. Also, the cells can be used to generate monoclonal antibodies, which can then be employed to assess whether they preferentially bind to a given cell type. Correlation of antigenicity can confirm that the stem cell has differentiated along a given developmental pathway.

While the cell can be solitary and isolated from other cells, preferably it is within a population of cells, and the invention provides a defined population including the inventive cell. In some embodiments, the population is heterogeneous. Thus, for example, the population can include support cells for supplying factors to the inventive cells. Of course, the inventive stem cells can themselves serve as support cells for culturing other types of cells (such as other types of stem cells, e.g., as neural stem cells (NSC), hematopoetic stem cells (HPC, particularly CD34+ stem cells), embryonic stem cells (ESC) and mixtures thereof), and the population can include such cells. In other embodiments, the population is substantially homogeneous, consisting essentially of the inventive lipo-derived stem cells.

As the inventive cells can be cloned, a substantially homogeneous population containing them can be clonal. Indeed, the invention also pertains to any defined clonal cell population consisting essentially of mesodermal stem cells, connective tissue stem cell, or mixtures thereof. In this embodiment, the cells can be lipo-derived or derived from other mesodermal or connective cell tissues (e.g., bone marrow, muscle, etc.) using methods known in the art. After the isolation, the cells can be expanded clonally as described herein.

The inventive cells (and cell populations) can be employed for a variety of purposes. As mentioned, the cells can support the growth and expansion of other cell types, and the invention pertains to methods for accomplishing this. In one aspect, the invention pertains to a method of conditioning culture medium using the inventive stem cells and to conditioned medium produced by such a method. The medium becomes conditioned upon exposing a desired culture medium to the cells under conditions sufficient for the cells to condition it. Typically, the medium is used to support the growth of the inventive cells, which secrete hormones, cell matrix material, and other factors into the medium. After a suitable period (e.g., one or a few days), the culture medium containing the secreted factors can be separated from the cells and stored for future use. Of course, the inventive cells and populations can be re-used successively to condition medium, as desired. In other applications (e.g., for co-culturing the inventive cells with other cell types), the cells can remain within the conditioned medium. Thus, the invention provides a conditioned medium obtained using this method, which either can contain the inventive cells or be substantially free of the inventive cells, as desired.

The conditioned medium can be used to support the growth and expansion of desired cell types, and the invention provides a method of culturing cells (particularly stem cells) using the conditioned medium. The method involves maintaining a desired cell in the conditioned medium under conditions for the cell to remain viable. The cell can be maintained under any suitable condition for culturing them, such as are known in the art. Desirably, the method permits successive rounds of mitotic division of the cell to form an expanded population. The exact conditions (e.g., temperature, $CO_2$ levels, agitation, presence of antibiotics, etc.) will depend on the other constituents of the medium and on the cell type. However, optimizing these parameters are within the ordinary skill in the art. In some embodiments, it is desirable for the medium to be substantially free of the lipo-derived cells employed to condition the medium as described herein. However, in other embodiments, it is desirable for the lipo-derived cells to remain in the conditioned medium and co-cultured with the cells of interest. Indeed, as the inventive lipo-derived cells can express cell-surface mediators of intercellular communication, it often is desirable for the inventive cells and the desired other cells to be co-cultured under conditions in which the two cell types are in contact. This can be achieved, for example, by seeding the cells as a heterogeneous population of cells onto a suitable culture substrate. Alternatively, the inventive lipo-derived cells can first be grown to confluence, which will serve as a substrate for the second desired cells to be cultured within the conditioned medium.

In another embodiment, the inventive lipo-derived cells can be genetically modified, e.g., to express exogenous genes or to repress the expression of endogenous genes, and the invention provides a method of genetically modifying such cells and populations. In accordance with this method, the cell is exposed to a gene transfer vector comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode biologically active RNA (e.g., antisense RNA or a ribozyme). Thus, for example, the coding polynucleotide can encode a gene conferring resistance to a toxin, a hormone (such as peptide growth hormones, hormone releasing factors, sex hormones, adrenocorticotrophic hormones, cytokines (e.g., interferins, interleukins, lymphokines), etc.), a cell-surface-bound intracellular signaling moiety (e.g., cell adhesion molecules, hormone receptors, etc.), a factor promoting a given lineage of differentiation, etc. Of course, where it is desired to employ gene transfer technology to deliver a given transgene, its sequence will be known.

Within the expression cassette, the coding polynucleotide is operably linked to a suitable promoter. Examples of suitable promoters include prokaryotic promoters and viral promoters (e.g., retroviral ITRs, LTRs, immediate early viral promoters (IEp), such as herpesvirus IEp (e.g., ICP4-IEp and ICP0-IEp), cytomegalovirus (CMV) IEp, and other viral promoters, such as Rous Sarcoma Virus (RSV) promoters, and Murine Leukemia Virus (MLV) promoters). Other suitable promoters are eukaryotic promoters, such as enhancers (e.g., the rabbit β-globin regulatory elements), constitutively active promoters (e.g., the β-actin promoter, etc.), signal specific promoters (e.g., inducible promoters such as a promoter responsive to RU486, etc.), and tissue-specific promoters. It is well within the skill of the art to select a promoter suitable for driving gene expression in a predefined cellular context. The expression cassette can include more than one coding polynucleotide, and it can include other elements (e.g., polyadenylation sequences, sequences encoding a membrane-insertion signal or a secretion leader, ribosome entry sequences, transcriptional regulatory elements (e.g., enhancers, silencers, etc.), and the like), as desired.

The expression cassette containing the transgene should be incorporated into a genetic vector suitable for delivering the transgene to the cells. Depending on the desired end application, any such vector can be so employed to genetically modify the cells (e.g., plasmids, naked DNA, viruses such as adenovirus, adeno-associated visus, herpesviruses, lentiviruses, papillomaviruses, retroviruses, etc.). Any method of constructing the desired expression cassette within such vectors can be employed, many of which are well known in the art (e.g., direct cloning, homologous recombination, etc.). Of course, the choice of vector will largely determine the method used to introduce the vector into the cells (e.g., by protoplast fusion, calcium-phosphate precipitation, gene gun, electroporation, infection with viral vectors, etc.), which are generally known in the art.

The genetically altered cells can be employed as bioreactors for producing the product of the transgene. In other embodiments, the genetically modified cells are employed to deliver the transgene and its product to an animal. For example, the cells, once genetically modified, can be introduced into the animal under conditions sufficient for the transgene to be expressed in vivo.

In addition to serving as useful targets for genetic modification, many cells and populations of the present invention secrete hormones (e.g., cytokines, peptide or other (e.g., monobutyrin) growth factors, etc.). Some of the cells naturally secrete such hormones upon initial isolation, and other cells can be genetically modified to secrete hormones, as discussed herein. The cells of the present invention that secrete hormones can be used in a variety of contexts in vivo and in vitro. For example, such cells can be employed as bioreactors to provide a ready source of a given hormone, and the invention pertains to a method of obtaining hormones from such cells. In accordance with the method, the cells are cultured, under suitable conditions for them to secrete the hormone into the culture medium. After a suitable period of time, and preferably periodically, the medium is harvested and processed to isolate the hormone from the medium. Any standard method (e.g., gel or affinity chromatography, dialysis, lyophilization, etc.) can be used to purify the hormone from the medium, many of which are known in the art.

In other embodiments, cells (and populations) of the present invention secreting hormones can be employed as therapeutic agents. Generally, such methods involve transferring the cells to desired tissue, either in vitro (e.g., as a graft prior to implantation or engrafting) or in vivo, to animal tissue directly. The cells can be transferred to the desired tissue by any method appropriate, which generally will vary according to the tissue type. For example, cells can be transferred to a graft by bathing the graft (or infusing it) with culture medium containing the cells. Alternatively, the new cells can be seeded onto the desired site within the tissue to establish a population. Cells can be transferred to sites in vivo using devices such as catherters, trocars, cannulae, stents (which can be seeded with the cells), etc. For these applications, preferably the cell secretes a cytokine or growth hormone such as human growth factor, fibroblast growth factor, nerve growth factor, insulin-like growth factors, hemopoetic stem cell growth factors, members of the fibroblast growth factor family, members of the platelet-derived growth factor family, vascular and endothelial cell growth factors, members of the TGFb family (including bone morphogenic factor), or enzymes specific for congenital disorders (e.g., distrophin).

In one application, the invention provides a method of promoting the closure of a wound within a patient using such cells. In accordance with the method, the inventive cells secreting the hormone are transferred to the vicinity of a wound under conditions sufficient for the cell to produce the hormone. The presence of the hormone in the vicinity of the wound promotes closure of the wound. The method promotes closure of both external (e.g., surface) and internal wounds. Wounds to which the present inventive method is useful in promoting closure include, but are not limited to, abrasions, avulsions, blowing wounds, burn wounds, contusions, gunshot wounds, incised wounds, open wounds, penetrating wounds, perforating wounds, puncture wounds, seton wounds, stab wounds, surgical wounds, subcutaneous wounds, or tangential wounds. The method need not achieve complete healing or closure of the wound; it is sufficient for the method to promote any degree of wound closure. In this respect, the method can be employed alone or as an adjunct to other methods for healing wounded tissue.

Where the inventive cells secrete an angiogenic hormone (e.g., vascular growth factor, vascular and endothelial cell growth factor, etc.), they (as well as populations containing them) can be employed to induce angiogenesis within tissues. Thus, the invention provides a method of promoting neovascularization within tissue using such cells. In accordance with this method, the cell is introduced the desired tissue under conditions sufficient for the cell to produce the angiogenic hormone. The presence of the hormone within the tissue promotes neovascularization within the tissue.

Because the inventive stem cells have a developmental phenotype, they can be employed in tissue engineering. In this regard, the invention provides a method of producing animal matter comprising maintaining the inventive cells under conditions sufficient for them to expand and differentiate to form the desired matter. The matter can include mature tissues, or even whole organs, including tissue types into which the inventive cells can differentiate (as set forth herein). Typically, such matter will comprise adipose, cartilage, heart, dermal connective tissue, blood tissue, muscle, kidney, bone, pleural, splanchnic tissues, vascular tissues, and the like. More typically, the matter will comprise combinations of these tissue types (i.e., more than one tissue type). For example, the matter can comprise all or a portion of an animal organ (e.g., a heart, a kidney) or a limb (e.g., a leg, a wing, an arm, a hand, a foot, etc.). Of course, in as much as the cells can divide and differentiate to produce such structures, they can also form anlagen of such structures. At early stages, such anlagen can be cryopreserved for future generation of the desired mature structure or organ.

To produce such structures, the inventive cells and populations are maintained under conditions suitable for them to expand and divide to form the desired structures. In some applications, this is accomplished by transferring them to an animal (i.e., in vivo) typically at a sight at which the new matter is desired. Thus, for example, the invention can facilitate the regeneration of tissues (e.g., bone, muscle, cartilage, tendons, adipose, etc.) within an animal where the cells are implanted into such tissues. In other embodiments, and particularly to create anlagen, the cells can be induced to differentiate and expand into tissues in vitro. In such applications, the cells are cultured on substrates that facilitate formation into three-dimensional structures conducive for tissue development. Thus, for example, the cells can be cultured or seeded onto a bio-compatible lattice, such as one that includes extracellular matrix material, synthetic polymers, cytokines, growth factors, etc. Such a lattice can be molded into desired shapes for facilitating the development of tissue types. Also, at least at an early stage during such culturing, the medium and/or substrate is supplemented with factors (e.g., growth factors, cytokines, extracellular matrix material, etc.) that facilitate the development of appropriate tissue types and structures. Indeed, in some embodiments, it is desired to co-culture the cells with mature cells of the respective tissue type, or precursors thereof, or to expose the cells to the respective conditioned medium, as discussed herein.

To facilitate the use of the inventive lipo-derived cells and populations for producing such animal matter and tissues, the invention provides a composition including the inventive cells (and populations) and biologically compatible lattice. Typically, the lattice is formed from polymeric material, having fibers as a mesh or sponge, typically with spaces on the order of between about 100 $\mu$m and about 300 $\mu$m. Such a structure provides sufficient area on which the cells can grow and proliferate. Desirably, the lattice is biodegradable over time, so that it will be absorbed into the animal matter as it develops. Suitable polymeric lattices, thus, can be formed from monomers such as glycolic acid, lactic acid, propyl fumarate, caprolactone, hyaluronan, hyaluronic acid, and the like. Other lattices can include proteins, polysaccharides, polyhydroxy acids, polyorthoesthers, polyanhydrides, polyphosphazenes, or synthetic polymers (particularly biodegradable polymers). Of course, a suitable polymer for forming such lattice can include more than one monomers (e.g., combinations of the indicated monomers). Also, the lattice can also include hormones, such as growth factors, cytokines, and morphogens (e.g., retinoic acid, aracadonic acid, etc.), desired extracellular matrix molecules (e.g., fibronectin, laminin, collagen, etc.), or other materials (e.g., DNA, viruses, other cell types, etc.) as desired.

To form the composition, the cells are introduced into the lattice such that they permeate into the interstitial spaces therein. For example, the matrix can be soaked in a solution or suspension containing the cells, or they can be infused or injected into the matrix. A particularly preferred composition is a hydrogel formed by crosslinking of a suspension including the polymer and also having the inventive cells dispersed therein. This method of formation permits the cells to be dispersed throughout the lattice, facilitating more even permeation of the lattice with the cells. Of course, the composition also can include mature cells of a desired phenotppe or precursors thereof, particularly to potentate the induction of the inventive stem cells to differentiate appropriately within the lattice (e.g., as an effect of co-culturing such cells within the lattice).

The composition can be employed in any suitable manner to facilitate the growth and generation of the desired tissue types, structures, or anlagen. For example, the composition can be constructed using three-dimensional or sterotactic modeling techniques. Thus, for example, a layer or domain within the composition can be populated by cells primed for osteogenic differentiation, and another layer or domain within the composition can be populated with cells primed for myogenic and/or chondrogenic development. Bringing such domains into juxtaposition with each other facilitates the molding and differentiation of complex structures including multiple tissue types (e.g., bone surrounded by muscle, such as found in a limb). To direct the growth and differentiation of the desired stucture, the composition can be cultured ex vivo in a bioreactor or incubator, as appropriate. In other embodiments, the structure is implanted within the host animal directly at the site in which it is desired to grow the tissue or structure. In still another embodiment, the composition can be engrafted on a host (typically an animal such as a pig, baboon, etc.), where it will grow and mature until ready for use. Thereafter, the mature structure (or anlage) is excised from the host and implanted into the host, as appropriate.

Lattices suitable for inclusion into the composition can be derived from any suitable source (e.g., matrigel), and some commercial sources for suitable lattices exist (e.g., suitable of polyglycolic acid can be obtained from sources such as Ethicon, N.J.). Another suitable lattice can be derived from the acellular portion of adipose tissue—i.e., adipose tissue extracellular matrix matter substantially devoid of cells, and the invention provides such a lipo-derived lattice. Typically, such lipo-derived lattice includes proteins such as proteoglycans, glycoproteins, hyaluronins, fibronectins, collagens (type I, type II, type III, type IV, type V, type VI, etc.), and the like, which serve as excellent substrates for cell growth. Additionally, such lipo-derived lattices can include hormones, preferably cytokines and growth factors, for facilitating the growth of cells seeded into the matrix.

The lipo-derived matrix can be isolated form adipose tissue similarly as described above, except that it will be present in the acellular fraction. For example, adipose tissue or derivatives thereof (e.g., a fraction of the cells following the centrifugation as discussed above) can be subjected to sonic or thermal energy and/or enzymatic processed to recover the matrix material. Also, desirably the cellular fraction of the adipose tissue is disrupted, for example by treating it with lipases, detergents, proteases, and/or by mechanical or sonic disruption (e.g., using a homogenizer or sonicator). However isolated, the material is initially identified as a viscous material, but it can be subsequently treated, as desired, depending on the desired end use. For example, the raw matrix material can be treated (e.g., dialyzed or treated with proteases or acids, etc.) to produce a desirable lattice material. Thus the lattice can be prepared in a hyrated form or it can be dried or lyophilized into a substantially anhydrous form or a powder. Therafter, the powder can be rehydrated for use as a cell culture substrate, for example by suspending it in a suitable cell culture medium. In this regard, the lipo-derived lattice can be mixed with other suitable lattice materials, such as described above. Of course, the invention pertains to compositions including the lipo-derived lattice and cells or populations of cells, such as the inventive lipo-derived cells and other cells as well (particularly other types of stem cells).

As discussed above, the cells, populations, lattices, and compositions of the invention can be used in tissue engineering and regeneration. Thus, the invention pertains to an implantable structure (i.e., an implant) incorporating any of these inventive features. The exact nature of the implant will vary according to the use to which it is to be put. The implant can be or comprise, as described, mature tissue, or it can include immature tissue or the lattice. Thus, for example, one type of implant can be a bone implant, comprising a population of the inventive cells that are undergoing (or are primed for) osteogenic differentiation, optionally seeded within a lattice of a suitable size and dimension, as described above. Such an implant can be injected or engrafted within a host to encourage the generation or regeneration of mature bone tissue within the patient. Similar implants can be used to encourage the growth or regeneration of muscle, fat, cartilage, tendons, etc., within patients. Other types of implants are anlagen (such as described herein), e.g., limb buds, digit buds, developing kidneys, etc, that, once engrafted onto a patient, will mature into the appropriate structures.

The lipo-derived lattice can conveniently be employed as part of a cell culture kit. Accordingly, the invention provides a kit including the inventive lipo-derived lattice and one or more other components, such as hydrating agents (e.g., water, physiologically-compatible saline solutions, prepared cell culture media, serum or derivatives thereof etc.), cell culture substrates (e.g., culture dishes, plates, vials, etc.), cell culture media (whether in liquid or powdered form), antibiotic compounds, hormones, and the like. While the kit can include any such ingredients, preferably it includes all ingredients necessary to support the culture and growth of desired cell types upon proper combination. Of course, if desired, the kit also can include cells (typically frozen), which can be seeded into the lattice as described herein.

While many aspects of the invention pertain to tissue growth and differentiation, the invention has other applications as well. For example, the lipo-derived lattice can be used as an experimental reagent, such as in developing improved lattices and substrates for tissue growth and differentiation. The lipo-derived lattice also can be employed cosmetically, for example, to hide wrinkles, scars, cutaneous depressions, etc., or for tissue augmentation. For such applications, preferably the lattice is stylized and packaged in unit dosage form. If desired, it can be admixed with carriers (e.g., solvents such as glycerine or alcohols), perfumes, antibiotics, colorants, and other ingredients commonly employed in cosmetic products. The substrate also can be employed autologously or as an allograft, and it can used as, or included within, ointments or dressings for facilitating wound healing. The lipo-dived cells can also be used as experimental reagents. For example, they can be employed to help discover agents responsible for early events in differentiation. For example, the inventive cells can be exposed to a medium for inducing a particular line of differentiation and then assayed for differential expression of genes (e.g., by random-primed PCR or electrophoresis or protein or RNA, etc.).

As any of the steps for isolating the inventive stem cells or the lipo-derived lattice, the, the invention provides a kit for isolating such reagents from adipose tissues. The kit can include a means for isolating adipose tissue from a patient (e.g., a cannula, a needle, an aspirator, etc.), as well as a means for separating stromal cells (e.g., through methods described herein). The kit can be employed, for example, as a bedside source of stem cells that can then be re-introduced from the same individual as appropriate. Thus, the kit can facilitate the isolation of lipo-derived stem cells for implantation in a patient needing regrowth of a desired tissue type, even in the same procedure. In this respect, the kit can also include a medium for differentiating the cells, such as those set forth herein. As appropriate, the cells can be exposed to the medium to prime them for differentiation within the patient as needed. Of course, the kit can me used as a convenient source of stem cells for in vitro manipulation (e.g., cloning or differentiating as described herein). In another embodiment, the kit can be employed for isolating a lipo-derived lattice as described herein.

EXAMPLES

While one of skill in the art is fully able to practice the instant invention upon reading the foregoing detailed description, the following examples will help elucidate some of its features. In particular, they demonstrate the isolation of a human lipo-derived stem cell substantially free of mature adipocytes, the isolation of a clonal population of such cells, the ability of such cells to differentiate in vivo and in vitro, and the capacity of such cells to support the growth of other types of stem cells. The examples also demonstrate the isolation of a lipo-derived lattice substantially free of cells that is capable of serving as a suitable substrate for cell culture. Of course, as these examples are presented for purely illustrative purposes, they should not be used to construe the scope of the invention in a limited manner, but rather should be seen as expanding upon the foregoing description of the invention as a whole.

The procedures employed in these examples, such as surgery, cell culture, enzymatic digestion, histology, and molecular analysis of proteins and polynucleotides, are familiar to those of ordinary skill in this art. As such, and in the interest of brevity, experimental details are not recited in detail.

assessed for viability (using trypan blue exclusion) and cell number. Thereafter, they were plated at a density of about at about $1 \times 10^6$ cells/100 mm dish. They were cultured at 37° C. in DMEM+fetal bovine serum (about 10%) in about 5% $CO_2$.

The majority of the cells were adherent, small, mononucleic, relatively agranular fibroblast-like cells containing no visible lipid droplets. The majority the cells stained negatively with oil-red O and von Kossa. The cells were also assayed for expression of telomerase (using a commercially available TRAP assay kit), using HeLa cells and HN-12 cells as positive controls. Human foreskin fibroblasts and HN-12 heated cell extracts were used as negative controls. Telomeric products were resolved onto a 12.5% polyacrylamide cells and the signals determined by phosphorimaging. Telemeric ladders representing telomerase activity were observed in the adipose-derived stem cells as well as the positive controls. No ladders were observed in the negative controls.

Thus, these cells were not identifiable as myocytes, adipocytes, chondrocytes, osteocytes, or blood cells. These results demonstrate that the adipose-derived cells express telomerase activity similar to that previously reported for human stem cells.

Subpopulations of these cells were then exposed to the following media to assess their developmental phenotype:

| Adipogenesis | Osteogenesis | Myogenesis | Chondrogenesis |
| --- | --- | --- | --- |
| DMEM | DMEM | DMEM | DMEM |
| 10% FBS | 10% FBS | 10% FBS | 1% FBS |
| 0.5 mM IBMX | 5% horse serum | 5% horse serum | 6.25 µg/ml insulin |
| 1 µM dexamethasone | 0.1 µM dexamethasone | 50 µM hydrocortisone | 6.25 µg/ml transferrin |
| 10 µM insulin | 50 µM ascorbate-2-phosphate | 1% ABAM | 10 ng/ml TGFβ1 |
| 200 µM indomethacin | 10 mM β-glycerophosphate | | 50 nM ascorbate-2-phosphate |
| 1% ABAM | 1% ABAM | | 1% ABAM |

Example 1

This example demonstrates the isolation of a human lipo-derived stem cell substantially free of mature adipocytes.

Raw liposuction aspirate was obtained from patients undergoing elective surgery. Prior to the liposuction procedures, the patients were given epinephrine to minimize contamination of the aspirate with blood. The aspirate was strained to separate associated adipose tissue pieces from associated liquid waste. Isolated tissue was rinsed thoroughly with neutral phosphate buffered saline and then enzymatically dissociated with 0.075% w/v colagenase at 37° C. for about 20 minutes under intermittent agitation. Following the digestion, the collagenase was neutralized, and the slurry was centrifuged at about 260 g for about 10 minutes, which produced a multi-layered supernatant and a cellular pellet. The supernatant was removed and retained for further use, and the pellet was resuspended in an erythrocyte-lysing solution and incubated without agitation at about 25° C. for about 10 minutes. Following incubation, the medium was neutralized, and the cells were again centrifuged at about 250 g for about 10 minutes. Following the second centrifugation, the cells were suspended, and A population was cultured at high density in the chondrogenic medium for several weeks. Histological analysis of the issue culture and paraffin sections was performed with H&E, alcian blue, toludene blue, and Goldner's trichrome staining at 2, 7, and 14 days. Immunohistochemistry was performed using antibodies against chondroitin-4-sulfate and keratin sulfate and type II collagen. Qualitative estimate of matrix staining was also performed. The results indicated that cartilaginous spheroid nodules with a distinct border of perichondral cells formed as early as 48 hours after initial treatment. Untreated control cells exhibited no evidence of chondrogenic differentiation. These results confirm that the stem cells have chondrogenic developmental phenotype.

A population was cultured until near confluence and then exposed to the adipogenic medium for several weeks. The population was examined at two and four weeks after plating by colorimetric assessment of relative opacity following oil red-O staining. Adipogenesis was determined to be underway at two weeks and quite advanced at four weeks (relative opacity of 1 and 5.3, respectively). Bone marrow-derived stem cells were employed as a positive control, and these cells exhibited slightly less adipogenic potential (relative density of 0.7 and 2.8, respectively).

A population was cultured until near confluence and then exposed to the osteogeneic medium for several weeks. The population was examined at two and four weeks after plating by colorimetric assessment of relative opacity following von Kossa staining. Osteogenesis was determined to be underway at two weeks and quite advanced at four weeks (relative opacity of 1.1 and 7.3, respectively). Bone marrow-derived stem cells were employed as a positive control, and these cells exhibited slightly less osteogenic potential (relative density of 0.2 and 6.6, respectively).

A population was cultured until near confluence and then exposed to the myogenic medium for several weeks. The population was examined at one, three, and six weeks after plating by assessment of multinucleated cells and expressin of muscle-specific proteins (MyoD and myosin heavy chain). Human foreskin fibroblasts and skeletal myoblasts were used as controls. Cells expressing MyoD and myosin were found at all time points following exposure to the myogenic medium in the stem cell population, and the proportion of such cells increased at 3 and 6 weeks. Multinucleated cells were observed at 6 weeks. In contrast, the fibroblasts exhibited none of these characteristics at any time points.

These results demonstrate the isolation of a human lipo-derived pluripotent stem cell substantially free of mature adipocytes.

Example 2

This example demonstrates that lipo-derived stem cells do not differentiate in response to 5-azacytidine.

Lipo-derived stem cells obtained in accordance with Example 1 were cultured in the presence of 5-azacytidine. In contrast with bone marrow-derived stem cells, exposure to this agent did not induce myogenic differentiation (see Wakitani et al., supra).

Example 3

This example demonstrates the generation of a clonal population of human lipo-derived stem cells.

Cells isolated in accordance with the procedure set forth in Example 1 were plated at about 5,000 cells/100 mm dish and cultured for a few days as indicated in Example 1. After some rounds of cell division, some clones were picked with a cloning ring and transferred to wells in a 48 well plate. These cells were cultured for several weeks, changing the medium twice weekly, until they were about 80% to about 90% confluent (at 37° C. in about 5% $CO_2$ in ⅔ $F_{12}$medium+ 20% fetal bovine serum and ⅓ standard medium that was first conditioned by the cells isolated in Example 1, "cloning medium"). Thereafter, each culture was transferred to a 35 mm dish and grown, and then retransferred to a 100 mm dish and grown until close to confluent. Following this, one cell population was frozen, and the remaining populations were plated on 12 well plates, at 1000 cells/well.

The cells were cultured for more than 15 passages in cloning medium and monitored for differentiation as indicated in Example 1. The undifferentiated state of each clone remained true after successive rounds of differentiation.

Populations of the clones then were established and exposed to adipogenic, chondrogenic, myogenic, and osteogenic medium as discussed in Example 1. It was observed that at least one of the clones was able to differentiate into bone, fat, cartilage, and muscle when exposed to the respective media, and most of the clones were able to differentiate into at least three types of tissues. The capacity of the cells to develop into muscle and cartilage further demonstrates the pluripotentiality of these lipo-derived stem cells.

These results demonstrate that the lipo-derived stem cells can be maintained in an undifferentiated state for many passages without the requirement for specially pre-screened lots of serum. The results also demonstrate that the cells retain pluripotentiality following such extensive passaging, proving that the cells are indeed stem cells and not merely committed progenitor cells.

Example 4

This example demonstrates the lipo-derived stem cells can support the culture of other types of stem cells.

Human lipo-derived stem cells were passaged onto 96 well plates at a density of about 30,000/well, cultured for one week and then irradiated. Human $CD34^+$ hematopoetic stem cells isolated from umbilical cord blood were then seeded into the wells. Co-cultures were maintained in MyeloCult H5100 media, and cell viability and proliferation were monitored subjectively by microscopic observation. After two weeks of co-culture, the hematopoetic stem cells were evaluated for CD34 expression by flow cytometry.

Over a two-week period of co-culture with stromal cells, the hematopoetic stem cells formed large colonies of rounded cells. Flow analysis revealed that 62% of the cells remained CD34+. Based on microscopic observations, human adipo-derived stromal cells maintained the survival and supported the growth of human hematopoetic stem cells derived from umbilical cord blood.

These results demonstrate that stromal cells from human subcutaneous adipose tissue are able to support the ex vivo maintenance, growth and differentiation of other stem cells.

Example 5

This example demonstrates that the lipo-derived stem cells can differentiate in vivo.

Four groups (A–D) of 12 athymic mice each were implanted subcutaneously with hydroxyapatite/tricalcium phosphate cubes containing the following: Group A contained lipo-derived stem cells that had been pretreated with osteogenic medium as set forth in Example 1. Group B contained untreated lipo-derived stem cells. Group C contained osteogenic medium but no cells. Group D contained non-osteogenic medium and no cells. Within each group, six mice were sacrificed at three weeks, and the remaining mice sacrificed at eight weeks following implantation. The cubes were extracted, fixed, decalcified, and sectioned. Each section was analyzed by staining with H&E, Mallory bone stain, and immunostaining for osteocalcin.

Distinct regions of osteoid-like tissue staining for osteocalcin and Mallory bone staining was observed in sections from groups A and B. Substantially more osteoid tissue was observed in groups A and B than in the other groups ($p<0.05$ ANOVA), but no significant difference in osteogenesis was observed between groups A and B. Moreover, a qualitative increase in bone growth was noted in both groups A and B between 3 and 8 weeks. These results demonstrate that the lipo-derived stem cells can differentiate in vitro.

Example 6

This example demonsrates the isolation of a lipo-derived lattice substantially devoid of cells.

In one protocol withheld supernatant from Example 1 was subjected to enzymatic digestion for three days in 0.05% trypsin EDTA/100 U/ml deoxyribonuclease to destroy the cells. Every day the debris was rinsed in saline and fresh enzyme was added. Thereafter the material was rinsed in saline and resuspended in 0.05% collagease and about 0.1% lipase to partially digest the proteins and fat present. This incubation continued for two days.

In another protocol, the withheld supernatant from Example 1 was incubated in EDTA to eliminate any epithelial cells. The remaining cells were lysed using a buffer containing 1% NP40, 0.5% sodium deoxycholate, 0.1% SDS, 5 mM EDTA, 0.4M NaCl, 50 mMTris-HCL (pH 8) and protease inhibitors, and 10 µg/ml each of leupeptin, chymostatin, antipain, and pepstatin A. Finally, the tissue was extensively washed in PBS without divalent cations.

After both preparatory protocols, remaining substance was washed and identified as a gelatinous mass. Microscopic analysis of this material revealed that it contained no cells, and it was composed of high amounts of collagen (likely type IV) and a wide variety of growth factors. Preparations of this material have supported the growth of cells, demonstrating it to be an excellent substrate for tissue culture.

Incorporation by Reference

All sources (e.g., inventor's certificates, patent applications, patents, printed publications, repository accessions or records, utility models, world-wide web pages, and the like) referred to or cited anywhere in this document or in any drawing, Sequence Listing, or Statement filed concurrently herewith are hereby incorporated into and made part of this specification by such reference thereto.

Guide to Interpretation

The foregoing is an integrated description of the invention as a whole, not merely of any particular element of facet thereof. The description describes "preferred embodiments" of this invention, including the best mode known to the inventors for carrying it out. Of course, upon reading the foregoing description, variations of those preferred embodiments will become obvious to those of ordinary skill in the art The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

As used in the foregoing description and in the following claims, singular indicators (eg., "a" or "one") include the plural, unless otherwise indicated. Recitation of a range of discontinuous values is intended to serve as a shorthand method of referring individually to each separate value falling within the range, and each separate value is incorporated into the specification as if it were individually listed Additionally, the following terms are defined as follows:

An anlage is a primordial structure that has a capacity to develop into a specific mature structure.

A developmental phenotype is the potential of a cell to acquire a particular physical phenotype through the process of differentiation.

A hormone is any substance that is secreted by a cell and that causes a phenotypic change in the same or another cell upon contact.

A stem cell is a pluripotent cell that has the capacity to differentiate in accordance with at least two discrete developmental pathways.

As regards the claims in particular, the term "consisting essentially of" indicates that unlisted ingredients or steps that do not materially affect the basic and novel properties of the invention can be employed in addition to the specifically recited ingredients or steps. In contrast, terms such as "comprising," "having," and "including" indicate that any ingredients or steps can be present in addition to those recited. The term "consisting of" indicates that only the recited ingredients or steps are present, but does not foreclose the possibility that equivalents of the ingredients or steps can substitute for those specifically recited.

We claim:

1. An isolated adipose-derived stem cell that can differentiate into two or more of the group consisting of a bone cell, a cartilage cell, a nerve cell, or a muscle cell.

2. An isolated, adipose-derived multipotent cell that differentiates into cells of two or more mesodermal phenotypes.

3. An isolated adipose-derived stem cell that differentiates into two or more of the group consisting of a fat cell, a bone cell, a cartilage cell, a nerve cell, or a muscle cell.

4. An isolated adipose-derived stem cell that differentiates into a combination of any of a fat cell, a bone cell, a cartilage cell, a nerve cell, or a muscle cell.

5. A substantially homogeneous population of adipose-derived stem cells, comprising a pluality of the stem cell of claim 1, 3 or 4.

6. The adipose-derived stem cell of claim 1, 3 or 4 which can be cultured for at least 15 passages without differentiating.

7. The adipose-derived stem cell of claim 1, 3 or 4 which is human.

8. The cell of any of claim 1, 3 or 4 which is genetically modified.

9. The cell of any of claim 1, 3 or 4, which has a cell-surface bound intercellular signaling moiety.

10. The cell of any of claim 1, 3 or 4, which secretes a hormone.

* * * * *

UNITED STATES PATENT AND TRADEMARK OFFICE
Certificate

Patent No. 6,777,231 B1

Patented: August 17, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Adam J. Katz, Charlottesville, VA (US); and Ramon Llull, Mallorca, (ES).

Signed and Sealed this Fifth Day of October 2010.

CHARLES S. LOW
*Supervisory Patent Examiner*
Art Unit 1636
Technology Center 1600

UNITED STATES PATENT AND TRADEMARK OFFICE
Certificate

Patent No. 6,777,231 B1                                                                        Patented: August 17, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Adam J. Katz, Charlottesville, VA (US); and Ramon Llull, Mallorca, (ES).

Signed and Sealed this Ninth Day of November 2010.

*CHRISTOPHER S. LOW*
*Supervisory Patent Examiner*
*Art Unit 1636*
*Technology Center 1600*